United States Patent [19]

Annis

[11] 4,366,576
[45] Dec. 28, 1982

[54] PENETRATING RADIANT ENERGY IMAGING SYSTEM WITH MULTIPLE RESOLUTION

[75] Inventor: Martin Annis, Cambridge, Mass.

[73] Assignee: American Science and Engineering, Inc., Cambridge, Mass.

[21] Appl. No.: 207,483

[22] Filed: Nov. 17, 1980

[51] Int. Cl.³ .............................................. G03B 41/16
[52] U.S. Cl. .................................... 378/146; 378/150
[58] Field of Search ............ 250/505, 511, 512, 445 T, 250/416 TV, 514

[56] References Cited

U.S. PATENT DOCUMENTS

4,031,401 6/1977 Jacob .................................... 250/514
4,260,898 4/1981 Annes .................................... 250/511

Primary Examiner—Craig E. Church
Attorney, Agent, or Firm—Pollock, Vande Sande & Priddy

[57] ABSTRACT

Penetrating radiant energy imaging system employs a scanning pencil beam of radiant energy. In some embodiments of the invention, the cross-section of the beam varies in a controlled manner; in a disclosed embodiment the beam has either one or another cross-section. A detector responds to incident radiant energy passing through a target and provides signals to a processor which produces from the signals a pair of image arrays, each array consisting of signals generated by the scanning pencil beam of one cross-section or the other. Increased contrast and/or resolution is provided by selectively combining the signals in the image arrays. In other embodiments of the invention, specifically related to tomographic imaging, rather than controlling the cross-section of the radiant energy at the source, the cross-section of the radiant energy is controlled at the detector field. In these embodiments, the detector field is occupied by multiple detectors and one or more of the detectors has a field of view which is different from the field of view of other detectors.

8 Claims, 11 Drawing Figures

PENETRATING RADIANT ENERGY IMAGING SYSTEM WITH MULTIPLE RESOLUTION

FIELD OF THE INVENTION

The invention relates to imaging systems using penetrating radiant energy, for example, such as X-rays, which are capable of producing, simultaneously, an image with relatively high spatial resolution in high contrast portions of the image along with the ability to detect low contrast portions of the image. The invention is applicable to conventional radiological imaging as well as to computed tomography.

BACKGROUND OF THE INVENTION

Prior art imaging systems using penetrating radiant energy illustrate a variety of architectures to achieve, within the constraints of practical realities, the ability to produce an image which accurately portrays the object being imaged while minimizing the radiation dose required to achieve that image. Two important characteristics play a large part in determining the accuracy with which an image portrays the object being imaged, those characteristics are the contrast and resolution of the image. Resolution is, of course, important so that objects being imaged can be precisely located, or in the case of relatively small objects, they can be even seen at all. Contrast is significant so that different materials within the object being imaged are portrayed as different.

One form of prior art penetrating radiant energy imaging systems, which are generally characterized as low dose systems, form a pencil beam of penetrating radiant energy which repeatedly scans a line in space at which a radiant energy detector is located, and the object being imaged is located between the source of the pencil beam and the detector. A single sweep of the pencil beam across the detector is then capable of producing a signal representative of the intensity of the radiant energy reaching the detector which can be correlated with the density of the portion of the object illuminated by the penetrating radiant energy. By providing relative motion between the X-ray source-detector combination with respect to the object being illuminated, different sweeps of the pencil beam can be made to scan different sections of the object being illuminated so that, over time, a raster type sweep of the object being illuminated is effected. Typically, the detector comprises an X-ray to electrical signal transducer, for example, a scintillation screen or crystal and photo multiplier or photo diode, so that for each sweep of the pencil beam across the detector, an electrical signal is produced. The electrical signal, as a function of time, represents the intensity of the impinging radiation and hence, the density of the object being illuminated, or that portion of the object illuminated during that particular sweep. These electrical signals can be used to directly generate a video image or can be stored, for example, by sampling, A/D converting and storage in a computer system. The computer system (which may comprise a mini-computer or microprocessor) is advantageous since it can retain the signals for convenient display at any time, and can also provide for processing of the signal so as to provide for various types of image enhancement.

A perennial problem in all types of radiant energy imaging is a desire to maximize resolution and contrast. Typically, it is difficult to achieve both simultaneously. In the pencil beam type systems these competing considerations require a choice to be made respecting the cross-section of the pencil beam (which typically establishes resolution) and amount of the detected X-ray flux (which typically establishes contrast). Decreasing the size of the pencil beam increases the resolution but decreases the contrast. Resolution seems to be achievable only at the direct expense of contrast, and vice versa. Examples of prior suggestions relating to the relationship between contrast, resolution and pencil beam cross-section are found in Annis et al Ser. No. 900,380 filed Apr. 26, 1978 (as a C.I.P. of Ser. No. 782,972, filed Mar. 30, 1977) and Annis Ser. No. 946,913 filed Sept. 28, 1978 (as a continuation of Ser. No. 782,973, filed Mar. 30, 1977). In both these applications a scanning pencil beam imaging device is disclosed which can develop an image using one of plural possible pencil beam cross-sections. In other types of radiant energy imaging, these competing considerations take different forms, however, maintaining dosage reasonably constant, one can only maximize resolution at the expense of contrast, and vice versa.

It is a specific object of the present invention to improve radiant energy imaging systems which employ a scanning pencil beam of penetrating radiant energy to improve the resolution without significantly sacrificing contrast and/or improve contrast without significantly sacrificing resolution. It is another object of the invention to provide a system which meets the foregoing objects of the invention and which has utility as well in computed tomography imaging systems.

SUMMARY OF THE INVENTION

In accordance with one aspect of the invention these and other objects of the invention are met by providing a penetrating radiant energy imaging system comprising a source of penetrating radiant energy, means for forming a sweeping pencil beam of penetrating radiant energy for repeatedly sweeping the beam across a detector field, beam cross-section control means to control the cross-section of the pencil beam between at least a first smaller cross-section and a second larger cross-section, the change in beam cross-section is effected in a fixed pattern as the beam illuminates an object in said detector field;

detector means located at said detector field for generating signals relating to the intensity of said beam impinging on said detector means, processor means responsive to said signals from said detector means for separately identifying sets of signals produced by beams of different cross-section and for developing from said sets of signals an image array corresponding to each of said pencil beams of different cross-section, and display means for developing an image and driven by said processor means.

In one specific embodiment of the invention a source of penetrating radiant energy is arranged adjacent to a collimator which produces a fan beam, a rotating drum is arranged so that the fan beam is incident on a surface of the drum. The surface of the drum includes at least two different slits spaced circumferentially apart so that the fan beam intercepts only one slit at a time as the drum rotates. The slits are dimensioned so that one of the slits describes a first smaller cross-section and the other of said slits describes a larger cross-section. A detector is located, spaced from said drum so that as the drum rotates the scanning pencil beam of penetrating radiant energy emitted from either of the slits scans across said detector. The detector is arranged to generate a signal which is related to the intensity of the beam impinging on the detector, so that when an object is positioned between the rotating drum and the detector, the electrical signal describes the radiant energy passing through said object in the path of said scanning pencil beam. Preferably, the X-ray source/detector is arranged for motion relative to the object being scanned in a direction perpendicular to the scanning motion of the pencil beam. Electrical signals produced by the detector are coupled to a processor for sampling, A/D conversion and storage. Preferably, a time base generator distinguishes, at the processor, signals related to pencil beams of larger and smaller cross-section and the processor is arranged to separately store signals corresponding to larger and smaller cross-section pencil beams so that the processor develops in image array corresponding to each of the pencil beams of different cross-section. And finally, a display means is arranged to be driven by the processor so as to display a suitable image.

In accordance with this aspect of the invention, the cross-sections of the pencil beams produced by the rotating drum are selected so that the larger cross-section pencil beam generates an image which can be characterized as displaying superior contrast resolution, but inferior spatial resolution whereas the image array developed by signals corresponding to the smaller cross-section pencil beam can be characterized as exhibiting superior spatial resolution and inferior contrast resolution. In one specific embodiment of the invention, these images can be combined for display purposes by simply summing them.

In a significant variation on this specific embodiment of the invention, however, the magnitude of signals in a selected one of the image arrays is multiplied by a selected constant before combining the image arrays so that one of the images is selectively enhanced compared to the other. Specifically, the magnitude of signals in the image array corresponding to the smaller pencil beam may be multiplied by a constant before combining the image arrays for display purposes.

Although a specific embodiment of the invention described above includes a pencil beam sweeping means comprising a collimator and a rotating drum, it is also within the scope of the invention to employ other forms of pencil beam sweeping means including, for example, a stationary plate with a single slit or any other device for forming a stationary sheet like (or fan like X-ray beam) and a rotating disc with different size slits at a common radial distance from the center of the disc, with slits spaced circumferentially apart by a sufficient amount to ensure that the fan beam of penetrating radiant energy emitted by the single slit impinges on only one rotating slit at a time.

As a further alternative the penetrating radiant energy transparent portion of the stationary member can take forms different than a slit, the rotating disc may have circular or rectangular holes rather than slits. In all of the foregoing embodiments of the invention the number of slits and/or holes can be increased from the two referred to, without necessarily maintaining equality between the number of slits of different sizes. That is, more particularly the holes or slits of one size may be greater in number than the holes and/or slits of another size.

The detector field preferably takes on a linear format, although in other embodiments of the invention the detector field can comprise arcs of a circle.

In other embodiments of the invention it is not essential that the display be produced as a result of combining the various image arrays but the image arrays can be employed alternately to produce a display such that a first display corresponds to a first image array and a second display corresponds to a second image array.

In addition, in some forms of tomographic imaging, rather than controlling the cross-section of the radiant energy at the source, cross-section of radiant energy is controlled at the detector field. In these forms of tomographic imaging the detector field is occupied by multiple detectors and one or more of the detectors has a field of view which is different from the field of view of other detectors.

As a further alternative the summing can be implemented in the optical domain, rather than using electrical signals.

THEORETICAL BASIS OF THE INVENTION

Before describing, in detail, specific embodiments of the invention, the manner in which contrast and/or resolution can be optimally adjusted will be explained in connection with a simplified example. Consider (refer to FIG. 1B) a source of penetrating radiant energy, for example, a rotating drum 31 intercepting a sheet or fan beam of X-rays from a suitable X-ray source, 11, 14 with slits A, B in the surface of the drum spaced circumferentially about the drum sufficiently far so that the X-rays intercept only a single slit at a time. Consider further that the surface of the drum has only two slits, one producing a pencil beam of square cross-section, a tenth millemeter on a side, and the other producing a pencil beam of square cross-section 1 mm on a side. Assume that this X-ray source is such that at the detector the number of photons due to the small hole with no object in the beam is $10^4/0.01$ mm$^2$ then the number of photons due to the large hole will be $10^8$/mm$^2$ with no object in the beam. Assume further that the pencil beam sweeps over a horizontally disposed detector field and further that the relative motion between X-ray source/detector and object being illuminated is such that each scan is separated from vertically adjacent scans by a center-to-center distance of 0.1 mm's, i.e., the upper edge of one small hole scan is directly adjacent the bottom edge of the immediately preceding small hole scan.

We define $F_s$ as the total number of photons at the detector in the area of the small hole (due to the small hole) and $F_L$ as the total number of photons at the detector in the area of the large hole (due to the larger hole). Since the holes define the dose as well as the resolution, defining the area of a small hole as $A_s$ and the area of the large holes as $A_L$, then $$F_s = \left( \frac{A_s}{A_L} \right)^2 F_L$$

and the number of photons in the area corresponding to the small hole at the detector due to the large hole, $F_L^s$ is $$F_L^s = \frac{A_s}{A_L} F_L;$$

-continued $$\left(\text{in the example } A_S/A_L = \frac{0.01 \text{ mm}^2}{1.0 \text{ mm}^2}\right) \text{ so}$$

$$F_s = \left(\frac{0.01}{1.0}\right)^2 \times 10^8 = 10^4 \text{ photons and}$$

$$F_L{}^s = \frac{0.01}{1.0} \times 10^8 = 10^6 \text{ photons}$$

Figure 4:
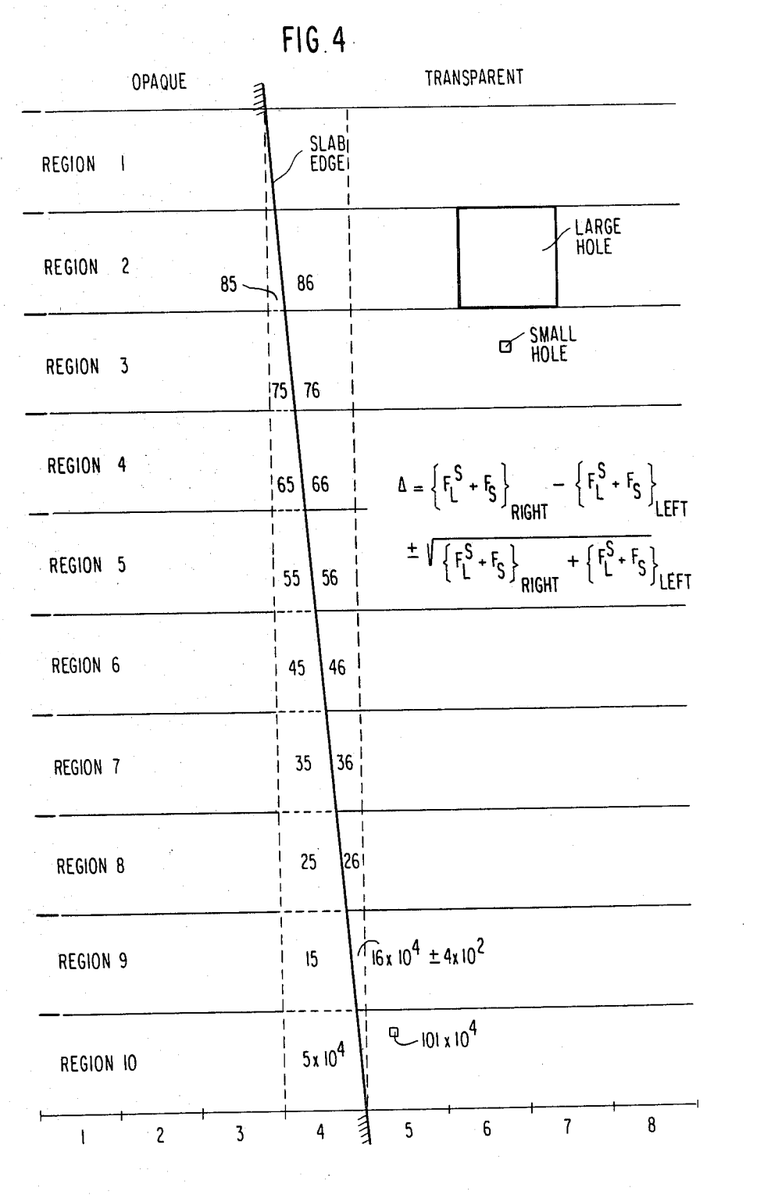
FIG. 4 is useful in explaining the theoretical basis of the invention.

To provide an example illustrating advantages of the invention assume that our exemplary pencil beam forming device is separated from the detector field by a slab which is perfectly opaque, i.e., that is no X-rays can pass through it, but past the edge of the slab we assume there is no impediment to the transmission of X-rays. For reasons which will appear hereinafter we will assume that the edge of the slab makes an angle with our detector field. Under these circumstances, FIG. 4 is a map of an image array which is produced by mapping for each sweep the X-ray energy incident on each small hole equivalent (0.01 mm²) area of the detector, and then aligning a second sweep vertically beneath the first, and so on. Alternatively, FIG. 4 can be considered to show the number of photons corresponding to the small hole dimension incident on each array location of dimension corresponding to the small slit.

The term $F_L{}^s$ is significant for when the larger cross-section pencil beam sweeps the detector, resolution is no better than 1 mm² and thus, some of the incident flux is "attributed" to locations in the image array "behind" the slab. The numbers to the right and left of the slab edge identify the number of photons per small square as the sum of photons due to large and small slits. We thus identify ten different regions, each region extending horizontally across the figure. The photons intercepted by each picture element or small square are made up of the appropriate proportion of photons incident by reason of passage of the large hole plus all or none of the photons incident by reason of passage of the small hole (we assume that fractions of the photons incident by reason of the passage of the small hole can safely be ignored). We then calculate the difference in photons per small square across the edge of the slab. For this purpose, in addition to identifying ten regions each extending horizontally across FIG. 4, we have broken down the abscissa into eight ports so that each region now has sub-regions of coordinate 1-8. Since the slab does not extend into any coordinate beyond the fourth, all sub-regions at or beyond coordinate 5 see $101 \times 10^4$ photons per small square element. This is merely the sum of the photons due to the small slit ($10^4$) plus the contribution in that small square due to the large hole ($10^8 \div 100 = 100 \times 10^4$). Since sub-regions of coordinate 3 or less are completely blocked by the slab, they see no photons at all. It is only sub-regions at coordinate in regions 1-10 which receive a variable amount of photons depending on which region they exist in.

Thus it is apparent why the slab edge is shown angled, if the edge were perfectly aligned vertically there would be no contribution from the large hole to areas to the left of the edge. This is not a practical difficulty since the slot dimensions (0.1 mm × 0.1 mm) are practical and very few, if any, real objects will have edges aligned or defined to this tolerance.

The number of photons impinging in the coordinate 4 sub-regions in regions 1-10 depends on the proportionate area to the right edge of the slab. Accordingly, the incident photons to the right of the slab edge varies from a minimum of $16 \times 10^4 \pm 4 \times 10^2$ photons per small square to a maximum of $101 \times 10^4 \div 10^3$ photons per small square. On the left, of the edge inputed incident flux varies from a minimum of $5 \times 10^4$ to a maximum of $85 \times 10^4$ photons per small square. Table 1, reproduced below, identifies the difference computed in accordance with the formula shown in FIG. 4, by region; inspection reveals that the difference averages almost $10^4$ photons per equivalent small square which is about 10 times the standard deviation (the square root of the number of detected photons).

TABLE I

PHOTONS PER SMALL SLIT AREA

| Region | To the Left | To the Right | Difference |
|---|---|---|---|
| 10 | $5 \times 10^4$ | $101 \times 10^4$ | $96 \times 10^4 \pm 10^3$ |
| 9 | $15 \times 10^4$ | $16 \times 10^4$ | $10^4 \pm 6 \times 10^2$ |
| 8 | $25 \times 10^4$ | $26 \times 10^4$ | $10^4 \pm 7 \times 10^2$ |
| 7 | $35 \times 10^4$ | $36 \times 10^4$ | $10^4 \pm 8 \times 10^2$ |
| 6 | $45 \times 10^4$ | $46 \times 10^4$ | $10^4 \pm 9 \times 10^2$ |
| 5 | $55 \times 10^4$ | $56 \times 10^4$ | $10^4 \pm 10^3$ |
| 4 | $65 \times 10^4$ | $66 \times 10^4$ | $10^4 \pm 11 \times 10^2$ |
| 3 | $75 \times 10^4$ | $76 \times 10^4$ | $10^4 \pm 12 \times 10^2$ |
| 2 | $85 \times 10^4$ | $86 \times 10^4$ | $10^4 \pm 13 \times 10^2$ |
| 1 | 0 | $96 \times 10^4$ | $96 \times 10^4 \pm 10^3$ |

In terms of a display, we could, using this data set a "level" at $55 \times 10^4$ photons per small square with a window at $20 \times 10^4$ photons per small square and accordingly the edge of the slab would be visible in 30 out of a hundred small squares, assuming the capability to detect 20 gray levels. Alternatively, the window could be set at $12 \times 10^4$ photons per small square and the edge would be seen in 20 out of 100 small squares assuming the ability to detect 12 gray levels, as the level is varied from $10^4$ to $85 \times 10^4$ photons per small square. Accordingly, the spatial resolution is about ±0.1 mm.

We can derive, at least intuitively, a formula for an approximation to the minimum size of the small hole, using the previously defined parameters as follows.

The total number of photons in a small square to the right of the edge is $$F_s + F_L{}^S = F_L \frac{A_s}{A_L}\left(1 + \frac{A_s}{A_L}\right)$$

The difference in photon number across the edge in the immediately adjacent small squares to the left and right of the edge (ignoring fractional squares) is:

$$\Delta = \{F_s + F_L{}^s\}_{Left} - \{F_L{}^s + F_s\}_{Right} \pm$$

$$\sqrt{\{F_L{}^s + F_s\}_{Left} + \{F_L{}^s + F_s\}_{Right}}$$

On the other hand, near the edge $$\Delta = F_s - 0 = F_s = \left(\frac{A_s}{A_L}\right)^2 F_L{}^I$$

Where $F_L{}^I$ is the incident flux through the large square, except when the edge of a large square happens to fall on the edge of the opaque plate. The standard deviation in this difference, $\sigma_\Delta$, is given by $$\sigma_\Delta =$$

$$\sqrt{\left\{F_L \frac{A_s}{A_L}\left(1 + \frac{A_s}{A_L}\right)\right\}_{right} + \left\{F_L \frac{A_s}{A_L}\left(1 + \frac{A_s}{A_L}\right)\right\}_{left}}$$

In general, $A_s/A_L << 1$ and $\left(F_L \frac{A_s}{A_L}\right)_{Right} = \left(F_L \frac{A_s}{A_L}\right)_{Left}$ in the worst case Therefore, $\sigma_\Delta = \sqrt{2 F_L^I \frac{A_s}{A_L}}$ The optimum size of the small square is somewhat larger than that given by the equation: $\sigma_\Delta/\Delta \approx 1$ or, $\dfrac{\sqrt{2 F_L^I \dfrac{A_s}{A_L}}}{\left(\dfrac{A_s}{A_L}\right)^2 F_L^I} = 1$ Thus, $$\frac{A_s}{A_L} = \left(\frac{2}{F_L^I}\right)^{\frac{1}{3}}$$

Using the previous example $F_L^I = 10^8$ photons and $A_L = 1.0 \times 1.0 = 1$ mm$^2$
so, $$\frac{A_s}{A_L} = \left(\frac{2}{10^8}\right)^{\frac{1}{3}} = 2.7 \times 10^{-3}$$

and $A_s = 2.7 \times 10^{-3}$ mm$^2$,
or $0.052 \times 0.052$ mm is the smallest value of the small square which results in improving the spatial resolution, at this exemplary flux level.

These and other equations included herein are based on statistical properties and the results of this and other equations are only a guide.

In a slightly more general case where $F_L^E$ is now the exit flux due to a single large square hole, $N_L$ is the number of large holes and $N_s$ is the number of small holes $$\frac{A_s}{A_L} = \left(\frac{2N_L^2}{N_s^2 N_L F_L^E}\right)^{\frac{1}{3}}$$

Taking a concrete example, for further illustration consider the application of the invention to conventional X-ray radiography in which an image is achieved by successively scanning each small projected area of the subject or patient using for example an AS&E X-ray MICRO DOSE system disclosed in U.S. Pat. Nos. 3,780,291 and 3,790,799, or the drum based imaging system found in U.S. Pat. No. 4,031,401. FIG. 1b is a schematic and as shown collimator 14 intercepts an X-ray beam to form a sheet or fan beam 15 of X-rays. This X-ray sheet or fan beam 15 is intercepted by a rotating drum 31 with radial slits every 90° (for example). The X-rays which traverse a slit form a narrow pencil beam 101 which moves rapidly across the subject in a direction determined by the direction of movement of the X-ray transmitting slit and impinges on detector 103. The sweeping action of the pencil beam provides for one direction of motion, and the other direction of motion is achieved by providing relative motion in the appropriate direction between the X-ray source/detector and the object being illuminated. Accordingly, the cross-section of the pencil beam is determined by the cross-section of the rotating slit.

Present day commercially available equipment has slits of identical width. In accordance with the present invention, however, one of the rotating slits has a width (or cross-section) which is narrower (or smaller) than the width (or cross-section) of the other rotating slits (s). For illustration, in connection with the geometry of U.S. Pat. No. 3,780,291 we assume that two of the rotating slits have a width of 0.4 mms and the other two have a width of 1 mm with a stationary slit having a width of 0.7 mm. Thus, the narrow rotating slits form a pencil beam of cross-section $0.4 \times 0.7$ mm or 0.28 mm$^2$, and the wider rotating slits form a beam of cross-section $1 \times 0.7$ mm or 0.7 mm$^2$.

For example, one complete rotation of the disc of U.S. Pat. No. 3,780,291 corresponds to relative motion between the source/detector and the object being illuminated of 0.7 mm. Thus, the pencil beam moves across the object four times, (once for each slit) during the same time the relative motion between object and source/detector moves a distance corresponding to the width of the stationary slit.

In order to achieve the advantages of the invention electrical signals corresponding to the narrow slits are summed in a position coherent sense to develop a signal array corresponding to an image, and similar processing is effected on the electrical signals corresponding to the larger slits so that a signal array is produced for each different cross-section beam.

Employing the previous parameters, the first signal array produces an image with superior spatial resolution and inferior contrast resolution, with a picture element size of $0.4 \times 0.7$ mm and a dose $r_1$.

The other signal array produces an image of inferior spatial resolution but superior contrast resolution with a picture element size $1 \times 0.7$ mm and a dose 2.5 times that of the first, i.e., 0.7 mm$^2$/0.28 mm$^2$.

Typically, the dose corresponding to the first image is 0.01 mR($2.5 \times 10^3$ photons/millimeter$^2$) and the higher dose corresponds to 0.25 mR (or $6.25 \times 10^3$ photons/millimeter$^2$).

To illustrate the advantages, assume further that a high contrast element of the image exhibited a 50% change in density for example, corresponding to a bone edge. The high spatial resolution image would receive $2.5 \times 10^3 \times 0.28$ (or $700 \pm 26$) photons on one side of the edge and half of that or $350 \pm 18$ photons on the other side of the edge. On the other hand, the low spatial resolution image would add photons to both picture elements approximately $2.5 \times 700$ or about $1750 \pm 42$ photons. As a result, adjacent high resolution picture elements would be subjected to $1750 + 700 \pm (42^2 + 26^2)^{\frac{1}{2}} = 2450 \pm 50$ photons, on one side of the edge and $1750 + 350 \pm (42^2 + 18^2)^{\frac{1}{2}} = 2100 \pm 46$ photons on the other side or a difference of $350 \pm 68$ photons. Since the intensity across this edge is more than 5 times the noise level ($68 \times 5 = 340$) the bone edge should be clearly discernable, assuming that the picture elements from each of the two images are added in a positionally coherent sense in that picture elements corresponding to like areas of the object illuminated are summed.

However, a further degree of freedom is the ability to amplify electronically one array of signals with respect to another. If there is no relative amplification, i.e., both signals are amplified by a like amount, the intensity of the small hole image array will be very low (although statistically significant) compared to the large hole image array. On the other hand, if the small hole signal array is amplified to make it equal to the large hole signal array, the statistical fluctuation in the small hole image will be very much larger than this statistical fluctuations in the larger hole image and as a result, the large hole image may very well disappear completely.

It is intuitively believed that there is an optimum setting for this relative amplification (of the small hole signal relative to the large hole) which is achieved when the small fluctuation ($\sigma_s$) is made smaller than the large hole fluctuation $\sigma_L$.

We can express the large hole fluctuation $\sigma_L$ as $$\left(\frac{A_s N_L F_L^E}{A_L}\right)^{\frac{1}{2}} \text{ and the small hole fluctuation (without}$$

relative amplication) is $$\sigma_s = (F_s)^{\frac{1}{2}} = \left(N_s \left(\frac{A_s}{A_l}\right)^2 F_L^E\right)^{\frac{1}{2}}$$

Using this notation the large hole signal is L and the (unamplified) small hole signal S, and these signals with their noise contribution are $L \pm \sigma_L$ and $S \pm \sigma_s$.

If we now apply relative amplification to the small hole signal of $a_s$, then this amplification should be no greater than the ratio of $$\sigma_L/\sigma_s$$

and so we can write that $$a_s \text{ is less than or equal to } \left(\frac{N_L A_L}{N_s A_s}\right)^{\frac{1}{2}}$$

For example, assuming that the area of the small hole is 100th of a square millimeter and there is one such hole, the area of the large hole is 1 square millimeter and there is one such hole, then the relative amplification should be less than or equal to 10.

APPLICATION OF THE INVENTION COMPUTED TOMOGRAPHY IMAGING

The field of computed tomography imaging can be conveniently divided into conventional computed tomography imaging exemplified by, for example, Stein et al application Ser. No. 726,556, filed Sept. 27, 1976, in which a fan beam emitting type X-ray source is provided with relative rotation with respect to an object to be illuminated, and also with respect to a plurality of X-ray detectors which may be located opposite the X-ray source with the object being imaged in the middle. The referred to application discloses a stationary ring detector is which the plurality of detectors are located circumferentially about the object being illuminated. The computed tomographic image is then created by correlating the radiant energy absorption in the object being illuminated with a plurality of directions from which the object is illuminated, so that a display illustrates a cross-section of a "slice" of the object being illuminated. While there are a variety of geometries in this class of computed tomography, many have in common the use of plural detectors. The other category of computed tomography equipment is that exemplified by the Swift application Ser. No. 150,823, filed May 10, 1980, the disclosure of which is hereby incorporated by reference. In Swift, the equipment shown in Stein U.S. Pat. No. 3,780,291 is employed for computed tomography by locating the object to be illuminated between the pencil beam source and detector, and then providing relative rotation between the source/detector and the object being illuminated; for ease of reference we shall refer to the first mentioned category of computed tomography devices as "conventional" and the latter mentioned device as Micro Dose computed tomography.

In applying the present invention in Micro Dose type computed tomography the pencil beam forming device is arranged so that it emits pencil beams of different cross-sections during imaging of an object, for example by the use of one or more narrow slits or holes and also wide slits or holes. In the fashion explained above, the detector response should be summed in a position coherent sense for the beams of different cross-section. Thus, an image array is created for each different beam cross-section. In addition, relative amplification of the small cross-section beam with respect to the large cross-section beam can be effected in a number of fashions, one relatively straight forward fashion is to change the gain of the detectors synchronously with slit rotation such that the detector gain is high (relatively) when the narrow slit emits a pencil beam (a small cross-section beam) and low (relatively) when the wide slit emits the pencil beam (larger cross-section).

Determination of relative slit sizes is, however, more complicated than for conventional radiography and in practice will be determined by practical factors such as relative sampling frequencies and artifacts caused by high sampling frequencies.

In connection with conventional computed tomography we must somehow alter the field of view of a number of the detectors, with respect to the other (unaltered) detectors. For example, for a stationary circular array, as exemplified by the aforementioned Stein application, every second, third or tenth detector has its field of view reduced by the use of collimating pins. However, it is also within the scope of the invention, rather than using merely two sizes of detectors, or detectors of two fields of view, to employ many sizes of detectors using different diameter collimating pins. In this application, as well as in the others mentioned above, relative gains can be adjusted to compensate for different areas.

Two motion scanners use the technique of the present invention in the case of "conventional" tomography.

BRIEF DESCRIPTION OF THE DRAWINGS

The present invention will now be further explained in the following portion of this specification when taken in conjunction with the attached drawings in which like reference characters identify identical apparatus and in which.

DETAILED DESCRIPTION

Figure 1A:
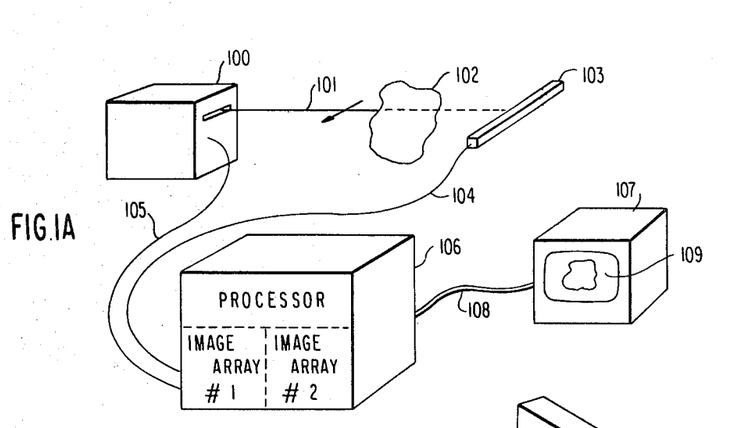
FIG. 1A is a block diagram of apparatus employing the invention in application to radiological imaging.
Figure 1B:
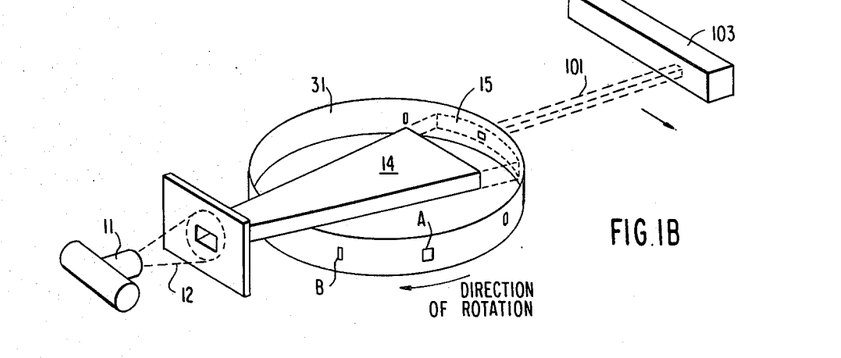
FIG. 1B is a schematic diagram of one form of sweep forming device 100 of FIG. 1A.

FIG. 1A is representation of apparatus arranged in accordance with the teaching of the present invention. As shown in FIG. 1A a sweeping means 100 is arranged for forming a pencil beam of penetrating radiant energy and repeatedly sweeping the pencil beam across a detector field, the sweeping means 100 includes a beam cross-section control means to control the cross-section of the pencil beam, represented at 101, between at least a first smaller cross-section and a second larger cross-section, the beam cross-section control means controlling the beam cross-section in a fixed pattern as the beam illuminates an object (such as object 102).

As the beam is swept repeatedly back and forth across the object 102, relative motion is imparted (by apparatus not shown) so that the sweeping means 100 and detector 103 move relative to the object 102 in a direction perpendicular to the scanning motion of the beam 101, in a fashion so as to develop a raster like sweep of the object 102. Penetrating radiant energy impinging on the detector 103 results in corresponding electrical signals which are coupled, via conductor 104 to a processor 106. The sweeping means 100 also includes a time base generator or synchronizing device which emits a signal to allow the processor 106 to identify signals corresponding to larger cross-section pencil beams or smaller cross-section pencil beams. The signal allowing this identification is coupled via the representative line 105 to the processor 106. The signal on line 105 can take a variety of forms, in the simple case where there is only one large hole and one small hole, the signal can be produced, by means well known in the art, to correlate with one or the other of the beams. If either the larger or smaller cross-section beam is produced via multiple holes whereas the beam cross-section of the other dimension is produced only once, then preferably this signal on line 105 is arranged to identify a signal which is produced only once. If beams of each cross-section are produced a multiple number of times, then the signal on line 105 can be arranged to be emitted corresponding to one of the beams or take on a distinctive form related to the beam cross-section. Alternatively, the signal can be produced once per cycle (to be defined) with processor 106 arranged to discriminate between beam cross-sections. Regardless of the manner in which the signal on line 105 is related to the larger or smaller cross-section beams, it should have sufficient information so that the processor 106 can identify electrical signals corresponding to the larger beam cross-section and separate those signals from electrical signals relating to the smaller beam cross-section.

The processor 106 receives and stores the signals in a position coherent sense in that each signal corresponds to a specific point in the raster sweep developed across the object 102, and the position coherence is maintained by the processor 106 so that as electrical signals are received via line 104, the processor 106 can develop an image array in which signals are stored so as to represent the X-ray absorbance or transmittance of the object 102. Significantly, the processor 106 develops an image array corresponding to each beam of different cross-section, thus for the embodiment of the invention which employs only beams of two different cross-sections, the processor 106 develops an image array corresponding to each of the beams.

Figure 5A:
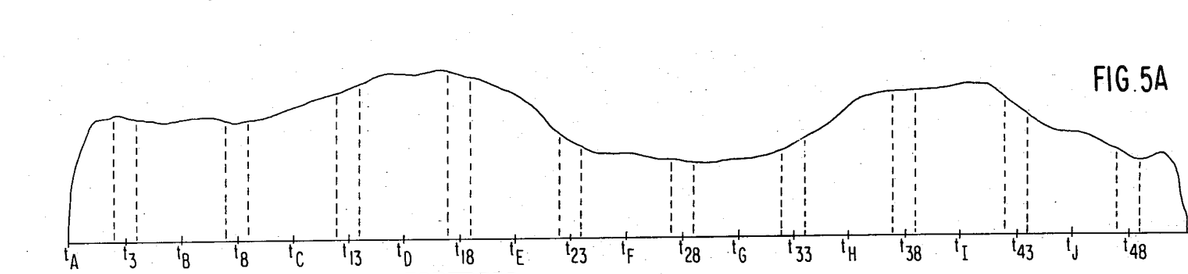
FIGS. 5A-5D are useful in illustrating the relation between signals corresponding to beams of different dimensions.
Figure 5B:
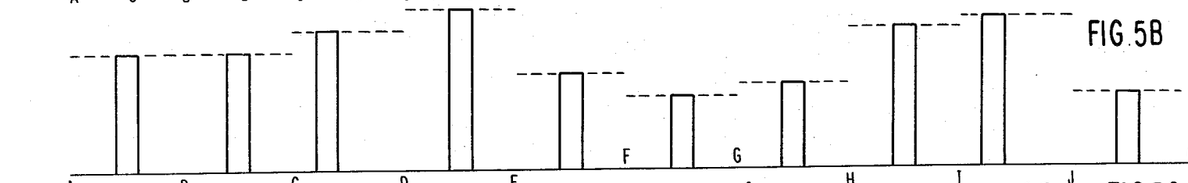
Figure 5C:
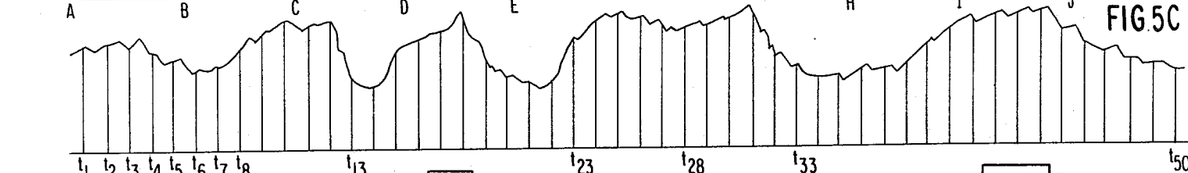
Figure 5D:
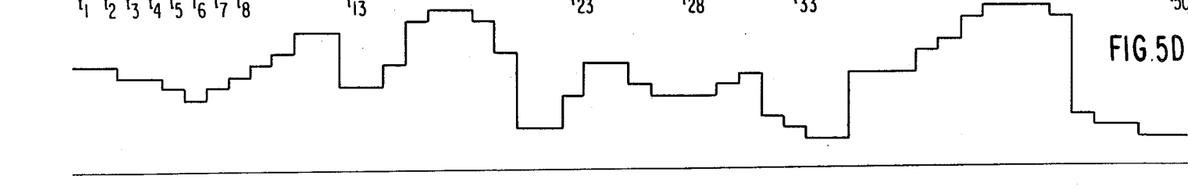

FIGS. 5A and 5C show typical signals which may be received corresponding to large and small beam cross-section, respectively. Since the large cross-section beam related signal has limited resolution, it may be sampled at times $t_3, t_8 \ldots t_{48}$ as shown. The samples are shown in FIG. 5B. The sample $t_3$ is attributed to the entire period $t_A$–$t_B$, likewise sample $t_8$ is attributed to the period $t_B$–$t_C$, and so on. Each of the periods $t_A$–$t_B$, $t_B$–$t_C$, etc., actually correspond to a specific area on the illuminated object, of width equal to the width of the pencil beam. Similarly the signal of FIG. 5C is also sampled, however, since the corresponding pencil beam is of smaller size, the sampling period is correspondingly shorter, thus, the small-cross section beam signal is sampled at times $t_1$–$t_{50}$. Each of the samples is attributed to the time (or area) between samples. In this case, of course the area is smaller, corresponding to the smaller beam cross-section. Let us assume that the area of the sweep shown in FIG. 5C is included in the area of the sweep of FIG. 5A, for example the sweep of FIG. 5C may directly precede (or follow) the sweep of FIG. 5A. A position coherent sum is shown in FIG. 5D. To effect this sum the entire area A–B is assumed to receive a contribution from the FIG. 5A signal equal to the sample at $t_3$, and each elemental portion of the A–B area also receives a contribution from the FIG. 5C sweep corresponding to the related sample. Of course, if desired the signal of FIG. 5C may be amplified prior to performing the summation. It should be apparent that each pencil beam generates an electrical signal on each sweep and thus the scan of the entire object produces a series of such signals. Each such signal is sampled and A/D converted and stored. Sampling may be accomplished at different rates for the sweeps of different cross-section, commensurate with the dimension of the beam although the large beam may be sampled at the higher (small beam) rate without loss of information. At the conclusion of the entire scan the series of electrical signals from each pencil beam has been converted to an array, which is representative of an image. One of the arrays may be amplified relative to the other, either during the original processing or subsequent to the entire scan. Each array can be used to generate a different image, or they can be summed, to generate a combined image.

Employing the image arrays, the processor 106, can via line 108, drive a display 107 so that the display 107 illuminates, on a screen 109 an image of the object 102. The two dimensions of the image correspond firstly to the scanning of the pencil beam 101 across the object, and secondly to the perpendicular relative motion between object 102 and the sweeping means 100/detector 103.

Figure 2:
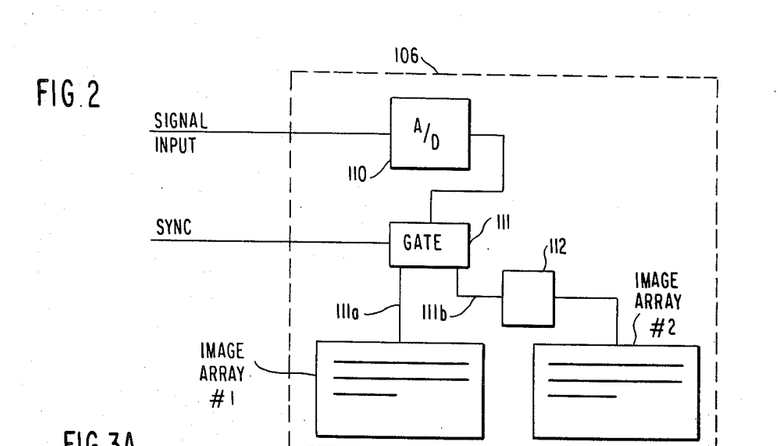
FIG. 2 is a functional block diagram of the processor 106 of FIG. 1A.

FIG. 2 is a functional representation of the operations carried on by the processor 106. As shown in FIG. 2, an A/D conversion function 110 is effected on the electrical signals from the detector 103. While the A/D conversion is shown as included in the processor 106, those skilled in the art will understand that A/D conversion can be effected external to the processor 106 by apparatus conventional in the art. The output of the A/D conversion function corresponds to a series of digital signals, each correlated with an electrical signal from either a large cross-section beam or small cross-section beam. These digital signals are input to a gate 111 having outputs 111a and 111b, each corresponding to beams of different cross-section. The other input to the gate is from the synchronizing signal derived from line 105 which can be used to identify a signal as relating to a large cross-section or small cross-section beam. The gate 111 thus directs the signals to its output 111a or 111b depending upon whether or not the signal relates to a large cross-section or small cross-section beam. Output 111a is employed to write a first image array, corresponding to one beam cross-section while output 111b is used to write image array number 2 corresponding to beams of the other size. As is discussed above, in accordance with one embodiment of the invention relative amplification is effected between image array number 1 and image array number 2, and as shown in FIG. 2, this relative amplification is effected by the multiplier 112. Those skilled in the art will understand that the multiplication or relative amplification function can be effected at any point in the signal chain from detector 103 onwards, so long as it is possible to discriminate between signals corresponding to large and small beam cross-section.

Significantly, FIG. 2 illustrates that the arrays develop simultaneously. This is for the reason that sweeps of beams of different cross-section are interleaved as opposed, for example, to scanning the object completely with a beam of one cross-section, and then starting again and scanning the object with a beam of another cross-section. This interleaving of sweeping of beams of different cross-section is dictated by the fact that the beam sweeping means, by its very construction necessarily produces a fixed relation between the number of beam sweeps of one cross-section and the number of beam sweeps of another cross-section, in any scanning of an object. Where the beam sweeping means includes only two holes or slits, one for each beam of different cross-section, then every other sweep will be effected with a beam of a different cross-section. On the other hand, if the beam sweeping means includes $N_L$ holes or slits of the larger cross-section and $N_S$ holes or slits of the smaller cross-section, then in any $N_L + N_S$ sequential sweeps (defined as a cycle), there will be $N_L$ sweeps by the beam of large cross-section, and $N_S$ sweeps of the beam of smaller cross-section. Furthermore, the order in which these different sweeps are effected is predetermined and fixed by the geometry of the beams sweeping means.

Beam sweeping means 100 can take any one of a variety of forms illustrated for example, in the drawings.

FIGS. 1B and 1C, and 3A-3B illustrate different forms of the beam sweeping means 100.

Referring now to FIG. 1B, a penetrating radiant energy source 11, comprising a source of X-rays, emits an X-ray beam 12 which may, for example, be cone-shaped which impinges on a collimator 14. Collimator 14 is triangular in plan view and rectangular in cross-section and emits a sheet or fan beam 15 of X-rays which impinge on the inner circumference of a drum 31. Spaced about the circumference of the drum 31 are a series of slits, at least one large slit A, and at least one small slit B. Adjacent slits are spaced circumferentially sufficiently far apart about the surface of drum 31 so that the fan shaped beam 15 intercepts only one slit at a time. Thus, as the drum 31 rotates in the direction shown, a pencil beam 101 is emitted which sweeps across a detector field, in which a detector 103 is located. The cross-section of the pencil beam 101 depends upon the dimensions of the operative slit, and the number of slits and their sizes can be chosen in the manner set forth above.

Figure 1C:
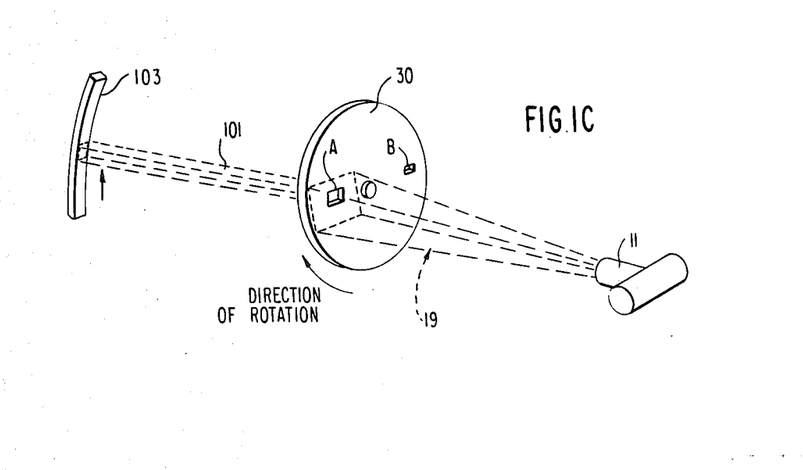
FIG. 1C is a schematic diagram of another form of sweep forming device 100 of FIG. 1A.

FIG. 1C illustrates a different arrangement for beam sweeping means 100. As shown in FIG. 1C X-ray source 11 emits an X-ray beam 19 which may be shaped in any convenient fashion so as to take on the characteristics shown in FIG. 1C. This beam impinges on a rotating disc 30, with at least one large slit A and at least one small slit B. As the disc 30 rotates in the direction illustrated, a pencil beam 101 is emitted which sweeps across a detector field occupied by X-ray detector 103. The cross-section of beam 101 which is emitted depends upon the dimensions of the operative slit. The disc 30 may carry one or more large slits A and one or more small slits B, with dimensions and number chosen in the manner described above. Adjacent slits are spaced sufficiently far apart circumferentially about the surface of the disc 30 so that only one slit at a time intercepts the beam 19.

Figure 3A:
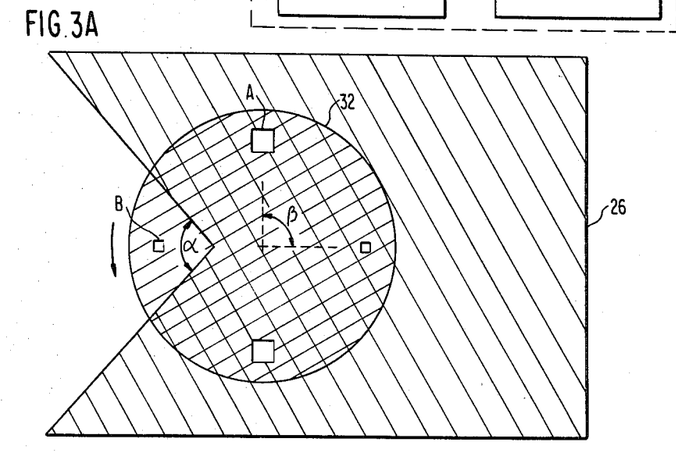
FIGS. 3A and 3B are plan and elevation views of still another beam forming device 100 of FIG. 1A.
Figure 3B:
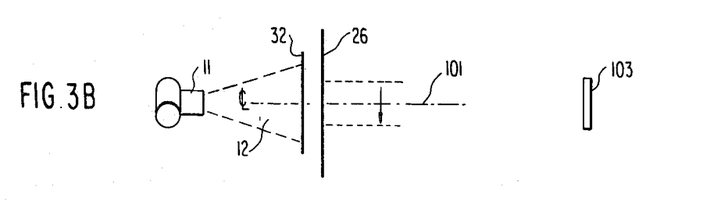

FIG. 3A shows a plane view of still a further arrangement for a beam sweeping means, and FIG. 3B illustrates an elevation thereof. As is shown in FIG. 3A a plate 26 of X-ray opaque material has a pie-shaped wedge removed therefrom. A rotating disc 32 is located in a plane parallel to the plane of the slab 26. The disc 32 carries, at a common radial distance from a center of rotation one or more large slits A and one or more small slits B. The slits are spaced sufficiently far apart circumferentially so that only one slit at a time can view the wedge-shaped cutout of the plate 26. Referring now to FIG. 3B, a source of X-rays 11 emits a beam 12 which impinges on the rotating disc 32. The beam is arranged so that its "spread" at the plate 32 is sufficient to allow it to be transmitted through the slits. Plate 26 however, stops pencil beams emitted by all the slits save the one in the vicinity of the cutout section of the plate 26. Accordingly, that particular slit only emits a pencil beam 101 which scans a detector 103. In the embodiment shown in FIGS. 3A and 3B, the pencil beam sweep is an arc of a circle, rather than a linear sweep. The angle $\alpha$ (see FIG. 3B) determines the angular distance over which the sweep is present. Use of arc-shaped detectors and fields is described in Annis, U.S. Pat. No. 4,228,357, assigned to the assignee of this application.

Although a number of different beam sweeping arrangements have been illustrated, those skilled in the art will be able to provide still other arrangements based upon the preceding description.

From the foregoing description of an embodiment of the invention applied to conventional radiological imaging, the application of the invention to Micro Dose tomography, should be apparent.

In application of the invention to conventional tomography we no longer have ready means of changing beam size. Rather, as disclosed above we change the field of view of certain detectors, and leave others unchanged. Thus, in conventional imaging and Micro Dose tomography the beam cross-section control is applied at the source of the scan but in conventional tomography the control is applied at the detectors. In either case the detector means generates interleaved signals corresponding respectively to beam cross-sections of different dimensions.

What is claimed is:

1. A penetrating radiant energy imaging system comprising:
   a source of penetrating radiant energy,
   sweeping means for forming a pencil beam of penetrating radiant energy for repeatedly sweeping said pencil beam across a detector field; beam cross-section control means to control the cross-section of said pencil beam between at least a first smaller cross-section and a second larger cross-section, in a fixed pattern, as said beam illuminates an object,
   detector means located at the detector field for generating signals related to the intensity of said beam impinging on said detector means,
   processor means responsive to said signals from said detector means for separately identifying sets of signals produced by beams of different cross-section and for developing from said signals an image array corresponding to each of said pencil beams of different cross-section, whereby an image array is developed for each pencil beam cross-section, and
   display means for developing an image in response to said processor means.

2. The apparatus of claim 1 in which said beam cross-section control means is associated with said sweeping means and in which said sweeping means includes a rotating radiant energy opaque member located in the path of said radiant energy for forming said pencil beam, said member including at least two radiant energy transparent locations, said at least two locations having different dimensions,
   whereby one of said transparent locations forms a pencil beam of a first smaller cross-section and another of said locations forms a pencil beam of a second larger cross-section as said member rotates said locations through a path of said radiant energy.

3. The apparatus of claim 2 in which said member includes N locations corresponding to said first smaller cross-section and M locations corresponding to said second larger cross-section, wherein N and M are unequal integers.

4. The apparatus of any of claims 2 or 3 wherein said member is a disc and each of said transparent locations are located at a common radial distance from an axis of rotation of said disc, and spaced circumferentially about said disc so that at any time only one of said locations forms a pencil beam.

5. The apparatus of any of claims 2 or 3 wherein said member is a drum and each of said transparent locations are located circumferentially about a surface of said drum so that at any time only one of said locations forms a pencil beam.

6. The apparatus of claim 3 in which locations corresponding to said smaller cross-section have a dimension $D_1$ and said locations corresponding to said larger cross-section have a dimension $D_2$, and wherein $D_1$ and $D_2$ depend on the intensity of said source, and said integers N and M.

7. The apparatus of any of claims 1–3 in which said processor means includes combining means to combine at least two of said image arrays for driving said display means.

8. The apparatus of claim 1 in which said detector means comprises a plurality of detectors and beam cross-section control means comprises at least a plurality of colliminating pins which limit the field of view of selected ones of said detectors.

* * * * *